(12) United States Patent
Balslev

(10) Patent No.: US 8,331,576 B2
(45) Date of Patent: Dec. 11, 2012

(54) METHOD FOR FITTING A BONE ANCHORED HEARING AID TO A USER AND BONE ANCHORED BONE CONDUCTION HEARING AID SYSTEM

(75) Inventor: Jens Balslev, Smørum (DK)

(73) Assignee: Oticon Medical A/S, Smorum (DK)

( * ) Notice: Subject to any disclaimer, the term of this patent is extended or adjusted under 35 U.S.C. 154(b) by 963 days.

(21) Appl. No.: 12/285,757

(22) Filed: Oct. 14, 2008

(65) Prior Publication Data

US 2009/0138062 A1 May 28, 2009

(30) Foreign Application Priority Data

Nov. 28, 2007 (EP) ..................................... 07121759

(51) Int. Cl.
*H04R 25/00* (2006.01)
(52) U.S. Cl. .......................................... 381/60; 381/314
(58) Field of Classification Search .................... 381/60; 600/25, 55
See application file for complete search history.

(56) References Cited

U.S. PATENT DOCUMENTS

| | | | | |
|---|---|---|---|---|
| 5,266,919 A * | 11/1993 | Cook et al. | ................. | 340/384.7 |
| 6,788,790 B1 | 9/2004 | Leysieffer et al. | | |
| 7,242,778 B2 * | 7/2007 | Csermak et al. | ................. | 381/60 |
| 7,258,671 B2 * | 8/2007 | Wasden | ........................ | 600/559 |
| 7,874,977 B2 * | 1/2011 | Pitulia | ............................. | 600/23 |
| 2004/0073135 A1 | 4/2004 | Wasden et al. | | |
| 2007/0195966 A1 * | 8/2007 | Fink et al. | ........................ | 381/60 |

OTHER PUBLICATIONS

Peder Carlsson et al. "Force Threshold for hearing by direct bone conduction", Journal of the Acoustical Society of America, vol. 97, No. 2, 1995, pp. 1124-1129.

* cited by examiner

*Primary Examiner* — Curtis Kuntz
*Assistant Examiner* — Amir Etesam
(74) *Attorney, Agent, or Firm* — Birch, Stewart, Kolasch & Birch, LLP

(57) ABSTRACT

The invention regards a method for programming a hearing aid wherein the hearing aid user is initially tested by subjecting the user to air borne sound and/or to bone transmitted vibrations, and based on the test results a bone conducting hearing threshold of a bone integrated bone conducting hearing aid is calculated, and further a bone conducting hearing aid is chosen and applied to a skin penetrating abutment which is firmly attached to a bone integrated fixture in the skull bone of the hearing aid user. According to the invention the vibrator in the chosen hearing aid is caused to vibrate at different frequencies and vibration levels and feed-back from the hearing aid user is obtained in order to obtain knowledge of the hearing aid users experienced hearing threshold with the attached hearing aid and finally the experienced hearing threshold is used to fine tune this same hearing aid for future wearing by the user.

12 Claims, 4 Drawing Sheets

METHOD FOR FITTING A BONE ANCHORED HEARING AID TO A USER AND BONE ANCHORED BONE CONDUCTION HEARING AID SYSTEM

AREA OF THE INVENTION

The invention relates to the area of hearing aid fitting and especially to a method of fitting a bone anchored hearing aid to the amplification needs of a hearing aid user.

BACKGROUND OF THE INVENTION

Traditionally hearing aid fitting is done by measuring audiogram by test tones of different frequencies and amplitude. In case the user needs a bone conductor hearing aid, an additional audiogram showing the bone-conducting-loss is to be measured. Both types of audiograms are measured in frequency steps of 5 dB's or 10 dB's. For air-conductive hearing aids, the typical sound tolerance spread between devices is about +/−3 dB at 1 kHz and +/−6 dB at frequencies below 500 Hz and above 2000 Hz.

Sometimes a "real-ear measurement" is performed to check if the client receives the prescribed gain. In this type of measurement, the precision of the results depends on the correct placement of a measurement tube, for a calibrated microphone, in the ear canal—together with the ITE-HA or ear mould of the BTE hearing aid. This measurement will give a good idea of the sound pressure, but may never be fully correct because of the extra leaky venting caused by the extra tube arranged in the ear.

All in all this leaves tolerances both on the supplied hearing aids and on the measurement type which means that the measures will never be as precise as wished. This is usually handled by a further subjective trimming, which is based on feed back on different listening situations obtained from the client.

The precision of the above fitting methods is based on measurement of the client's hearing threshold on traditionally calibrated equipment—but equipment which is not normally worn by the client.

Partially to handle this, it is known to use an internal tone generator in some hearing aids, by way of which an on-the-ear-audiogram can be obtained. This method of measuring the hearing threshold will be more precise with regards to compensating for the tolerances between devices. And also no venting issue is caused by the use of an audiometer microphone tube.

It is well known that performing bone-conduction (BC) audiometry is prone to large tolerances on the obtained results. The major reason for this is that traditional BC-audiometry is based on a measurement method which has built-in large inaccuracies.

Most of these measurements are done using a calibrated vibrator which is pressed to the skin and thus skull-bone—usually behind the ear. By providing well defined sinus tones of different levels and frequencies from the vibrator, the hearing threshold and/or uncomfortable level (UCL) can be measured by tracking reaction from the patient. However, this method is prone to inaccuracies due to the uneven attenuation of the skin—depending of pressure applied to the vibrator, and due to the slight frequency dependency on the transfer function of the skin, and also the ability to place the vibrators point of attack at exactly the same place each time. This also may be depending on which audiologist are attaching the vibrator to the head of the patient.

All in all, it is known that the total sum of these inaccuracies, in terms of repeatability, is in the range of 15-20 dB or even worse. This may cause patients with BC-losses to unintentionally get their hearing aids incorrectly fitted.

According to the invention it is attempted to assist in getting the best audiological fitting in order to help the patients to obtain an ossointegrated implant, which transfers the vibration from the BC hearing aid to the skull and thus to the cochlea in a way which best account for the hearing deficit of the user.

The idea is based on the fact that the fixed connection through the skin comprising implant and skin penetrating abutment is avoiding the uneven and placement-dependent attenuation of the skin and its texture. Also this provides the exact same point of vibration each time the BC-hearing aid is used. Thus a vibration applied to the implant will have same transfer-function of vibration to the cochlea each time used.

At the same time, bone-conductive hearing device may have a built-in sine generator which can be adjusted to all audiological relevant frequencies such as in the range from 200 Hz-10 kHz and precisely adjustable amplitude.

By combining this with a vibrator which has fairly small gain tolerances, well defined combinations of frequencies and amplitudes can be provided. This is very similar to a traditional BC-conductive audiometer but with expected applied amplitude accuracies about +/−2-3 dB. This means that an audiometric test can be done "on the patient" with more precise accuracy than earlier.

It is also known to use a calibrated vibrator in connection with a traditional audiometer. But such a calibrated vibrator is not the same as the one which the hearing aid user will finally wear after the fitting.

SUMMARY OF THE INVENTION

According to the invention, a hearing aid user is initially tested by subjecting the user to air borne sound and/or to bone transmitted vibrations, and based on the test results a bone conducting hearing threshold of a bone integrated bone conducting hearing aid is calculated, and further a bone conducting hearing aid is chosen and applied to a skin penetrating abutment which is firmly attached to a bone integrated fixture in the skull bone of the hearing aid user, and the vibrator in the chosen hearing aid is caused to vibrate at different frequencies and vibration levels and feed-back from the hearing aid user is obtained in order to obtain knowledge of the hearing aid users experienced hearing threshold with the attached hearing aid and finally the experienced hearing threshold is used to fine tune the same hearing aid which is the hearing aid the user will wear in the future.

By presenting the hearing aid user with different tones and amplitudes, the hearing threshold is determined. However, not in terms of exact values, but in terms of vibration level settings of the apparatus which the user will use in the future. In this way apparatus specific output characteristics such as variations in vibration levels within given tolerances of the apparatus, will not have any influence on the usefulness of the obtained results. Making the audiogram, using exactly the bone conduction hearing device which the patient is going to wear, will thereby cause the few dB's deviation from one bone conduction hearing aid to the next, to be included in the audiogram. Thus the patient gets his/her audiogram measured with the exact same hearing aid as he/she is going to wear. The benefit is a completely correct fitting of the patient.

In an embodiment of the invention the uncomfortable level of the hearing aid user is determined by causing the vibrator to vibrate at levels up to the uncomfortable level of the user.

This is only possible if high enough vibration levels are obtainable with the apparatus in question. However, only for a hearing aid apparatus which can reach this level of vibration will there be any reason in determining the uncomfortable level of the user.

Preferably, an internal programmable sine-generator in the osseo-integrated bone conductor hearing aid is used to produce the range of vibration frequencies and amplitudes used in the measurements of perceived levels of the user.

The vibration amplitude may not be accurate according to the setting chosen due to individual variations between the hearing aid apparatuses, but the essential thing is that the osseo integrated bone conductor hearing aid, due to the fixed mechanical attachment to the skull bone of the user, will generate a very precise and reproducible vibration level form day to day.

When the hearing aid is fitted according to the invention, the obtained audiogram will add the further benefit that it is checked, that the fitting gain provided on the skull and perceived by the user is in conformity with the calculated prescribed gain obtained prior to insertion of the implanted screw in the skull bone. The prescribed gain is calculated from the pre-surgery bone-conduction-audiometry and a standardized skin-vibration-loss curve.

The advantages obtained are among others:

When using the standardized skin-vibration-loss curve the audiogram may be flawed as different users may have different loss curves. The measurements performed according to the invention with the actual hearing aid in place will be independent of the pre-surgical audiometry and make a representation of the clients' own subjective perception of the hearing threshold and/or UCL and this may be different from the pre-surgical measures.

Once the hearing aid is in place, later adjustment—days/weeks/months/years after surgery—will be easier to do, and a new audiogram is obtainable just by connecting the programmable OBC to the fitting/audiometry software. No audiometry equipment is needed.

In a further embodiment of the invention the signal processor of the hearing aid comprises a memory space wherein an audiogram and corresponding hearing/UCL threshold will be saved for comparison with later obtained audiograms, in order to observe the changes in the clients hearing threshold.

In this way changes or deterioration of the sensorineural or conductive hearing losses of the user may be monitored safely, even if the user chooses to visit a second hearing clinic at a later time.

The number of frequency bands used in the measurement with the hearing aid may be increased to provide better fitting. The traditional 8-12 frequency band audiogram may not be sufficient, and further frequencies may be used.

In a further embodiment the measurement is made partly automated, in that the hearing aid is connected to a computer having a measurement program installed therein, and where input means to the computer are provided allowing the hearing aid user to press a first button when a sound is heard—or a second button if a sound is too loud.

In this way the testing of the hearing aid and user's perceived hearing level threshold with the hearing aid, may be performed automatically without supervision from a professional. This allows a more efficient process during fitting and fine-tuning of this kind of hearing aids.

The invention further concerns a bone anchored bone conduction hearing aid system comprising: a hearing aid; a vibrator in the hearing aid; a fixture anchored in the skull of a hearing aid user; the vibrator being connected to the skull bone via the fixture; the hearing aid unit having an electronic circuitry; a push button; the electronic circuitry having an input means operable to detect when the patient presses the push button; the electronic circuitry having an electronic memory; and the electronic circuitry having a tone generator and a program embedded in the electronic circuitry operable to perform audiometric measurements via the tone generator and the vibrator connected to the skull and where signal levels from the tone generator and the signals from the push button are storable within an electronic memory embedded in the electronic circuit.

By this bone anchored bone conduction hearing aid system it is very simple and straight forward to perform measurements with the apparatus itself when placed on the head of the user and connected to the skull bone.

Preferably the bone anchored bone conduction hearing aid system also comprises a push button, which is integrated in the hearing aid. This enables very simple feedback means between the user and the audiologist or computer system during measurements.

In an embodiment the bone anchored bone conduction hearing aid system transfer signals from the push button by wireless communication to the hearing aid or to the fitting computer system.

DESCRIPTION OF A PREFERRED EMBODIMENT

Figure 1:
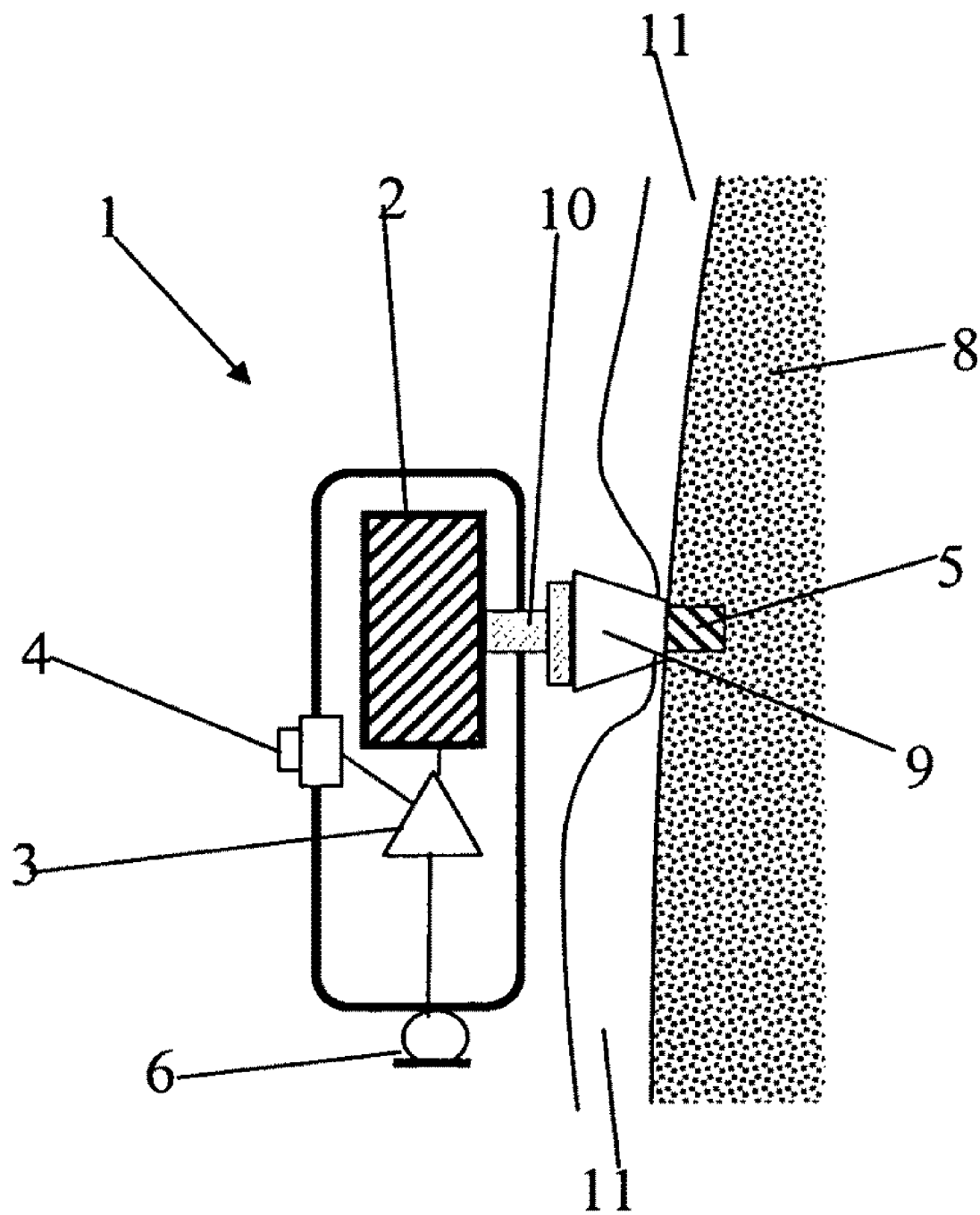
FIG. 1 shows a schematic representation of a hearing aid which may be used in accordance with the invention.

A hearing aid 1 which may be used according to the method of the invention is shown in FIG. 1. The hearing aid 1 comprises a vibrator 2, a signal processor and amplifier 3 and a microphone 6. As indicated in the figure, the signal from the microphone 6 is routed to the signal processor and amplifier 3 and a processed and amplified signal is served at the vibrator 2. The vibrator 2 is firmly attached to a screw 5 which is integrated into the skull bone 8 at the head of the user. Between the vibrator 2 and the screw 5, an abutment 9 is provided as well as a rod 10. The abutment 9 penetrates the skin 11 of the user and is firmly attached to the screw 5. The rod 10 is the output element from the vibrator 2 and is caused to vibrate according to the signal from the processor 3 and the vibrations are transmitted through the abutment 9 and screw 5 and into the skull bone 8 and from here into the inner ear (not shown) of the user where the vibrations are perceived as sound. In the inner ear the vibrations are perceived as sounds. The hearing aid 1 may have a push button 4 allowing the user to choose between programs, such as between directional and omni-directional processing in the hearing aid 1. Also this push button 4 may be used during measurement with the hearing aid.

The hearing aid 1 will further have a wired or wireless connection (not shown in FIG. 1) with a fitting tool, usually a computer 12 whereby the hearing aid 1 may be programmed to deliver output vibration levels in dependency of frequency according to the special needs of the individual user.

Figure 4:
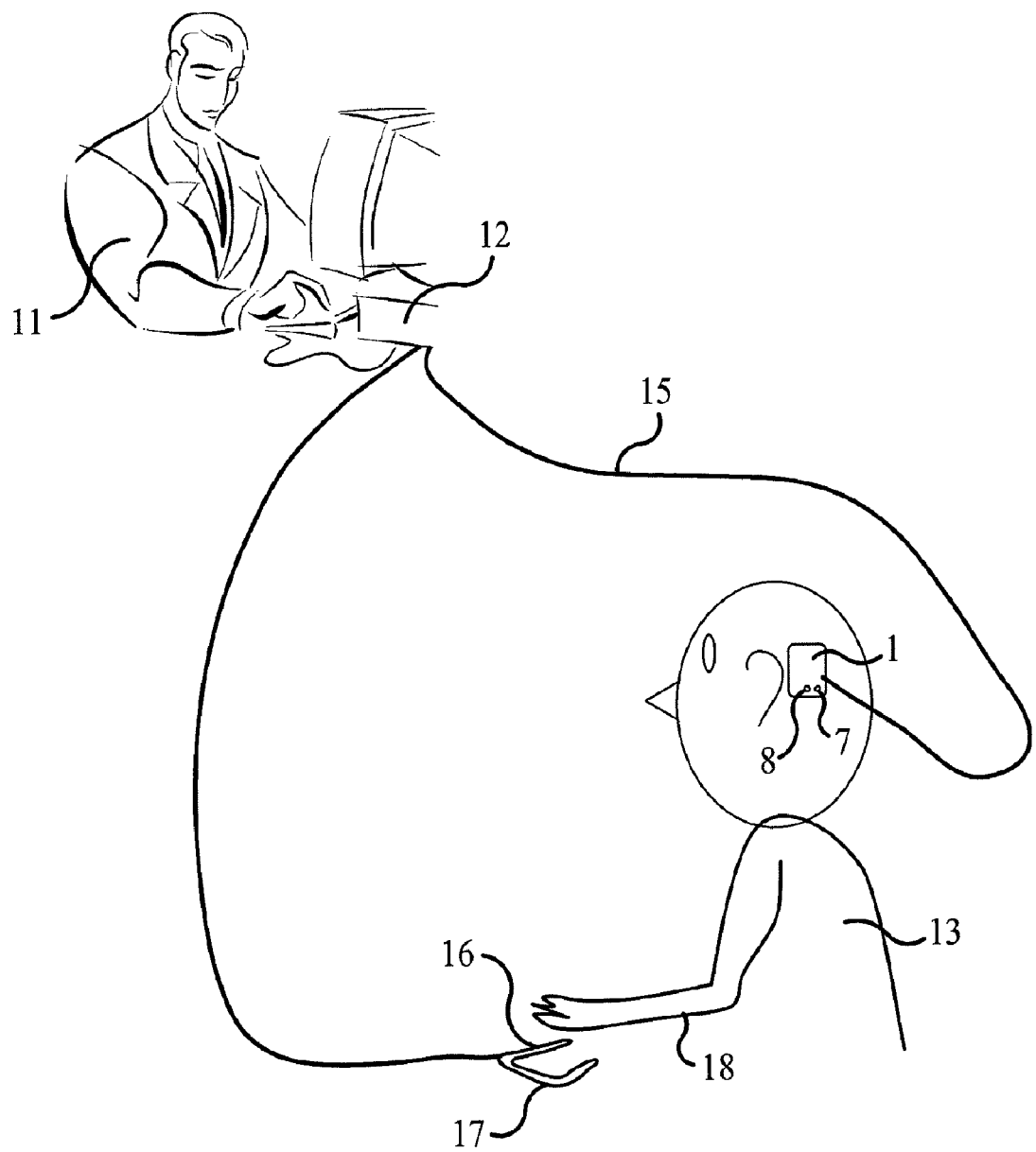
FIG. 4 shows a schematic representation of the fitting situation.

As of FIG. 4, an operator 11 such as an audiologist or an ear surgeon or an ENT may program and adjust the internal sine-generator of the hearing aid 1 to deliver different tones/ frequencies and levels and receive feedback from the hearing aid user 13. Just as a usual audiogram measurement, but with higher accuracy.

In FIG. 4 a programming cable 15 is displayed between the computer 12 and the hearing aid 1, but also a wireless connection may be used. By the connection 15 sound-tones may be generated by a tone generator inside the signal processor of the hearing aid 1 and transmitted to the user 13 through the vibrator 2.

The audiometer test may be conducted through the use of pushbuttons 16; 17 which the user may operate by hand 18 in order to acquire the patient's reaction when sound is audible or too loud. Also the push button 4 on the hearing aid shown in FIG. 1 may be used for giving feedback to the audiologist, the computer 12, or to a memory element in the electric circuitry of the hearing aid dependent on whether the user hears a tone or not.

The audiometer program in the computer 12 may be automatic or semi-automatic and provide tones and levels and react to the response of the patient's push on one of the buttons 16; 17. In this way the audiometer test need not be supervised by any third person 11 as displayed but may be performed by the computer and hearing aid user alone.

The room in which the measurements are done will require low noise especially for patients with single sided hearing loss. For patients with double sided hearing loss almost any sound environment may be used, as the microphone signal may be shut off while the hearing-level measurements are done.

An alternative—but less precise method could be used: By programming of the bone conducting hearing aid to have specific maximum output levels (ie output AGC set to specific level). Provide relatively high levels of audiometer tones to the microphones of the hearing aid. This will cause specific levels of that specific tone on the vibrator for the patient to react at.

This is alternative to use of the internal generator, but the accuracy of the transfer function from the hearing aid to the cochlea is the same.

Above it is explained that the vibration frequencies and levels are generated through the tone generator of the hearing aid 1 or from an audiometer, but it is also possible to provide the tones to the hearing aid 1 via a Direct Audio Input (DAI) which is an auxiliary sound input. Also a telecoil may be used as input for the test tones. The frequencies and levels are in these cases generated in the computer 12.

Figure 2:
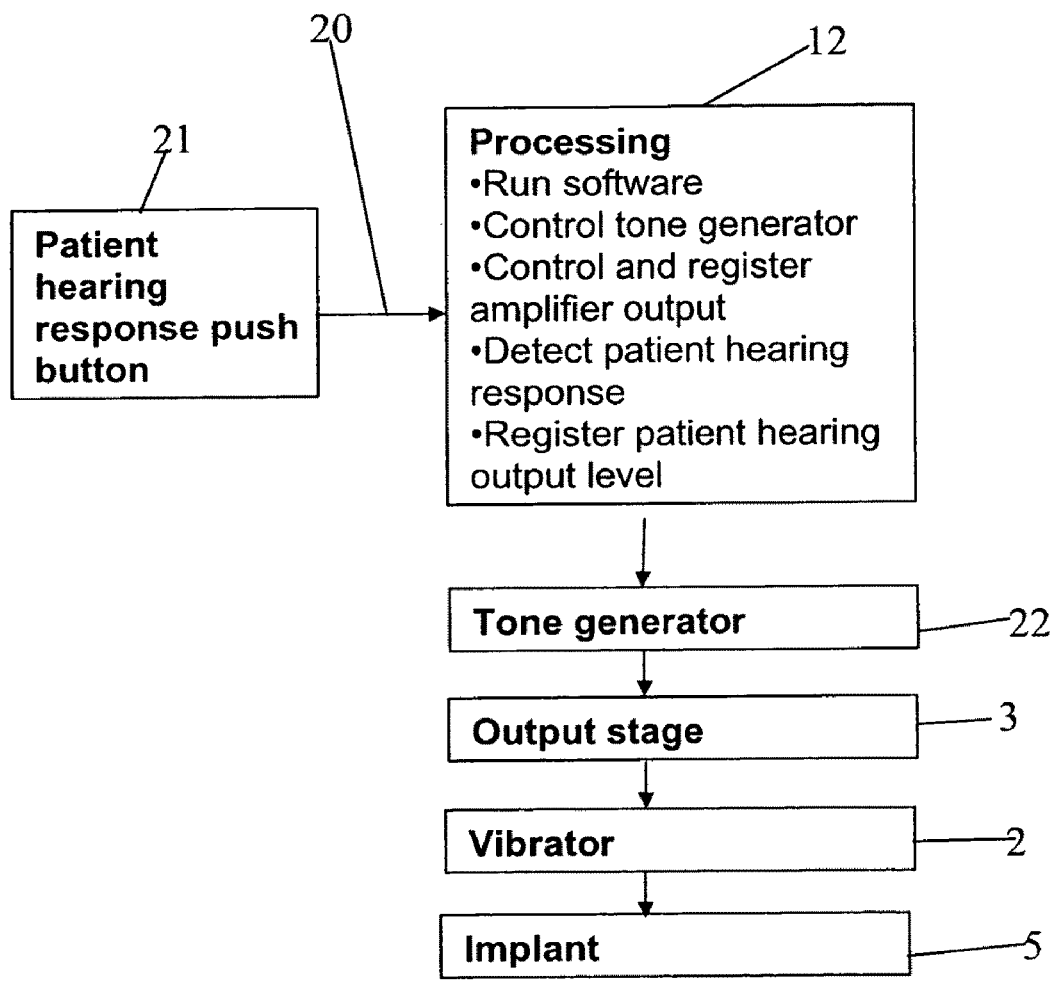
FIG. 2 shows a block diagram of a fine tuning process.

In FIG. 2 a schematic representation of the measurement is provided. The patient response 21 is captured by either push buttons or through direct feedback to the audiologist 11 and input to the computer 12 as indicated by arrow 20. On computer 20 a patient/hearing aid test software is running, whereby a tone generator either in the computer or in the hearing aid is controlled, and the settings thereof is registered along with the patient input at line 20. The tone generator 22 is caused to deliver a signal to the output stage 3 of the signal generator which causes the vibrator 2 to deliver vibrations at a specific frequency and level to the implanted screw 5. The software in computer 12 will then collect corresponding pairs of user response and output level settings at a number of frequencies and this is interpretable as an audiogram.

Figure 3:
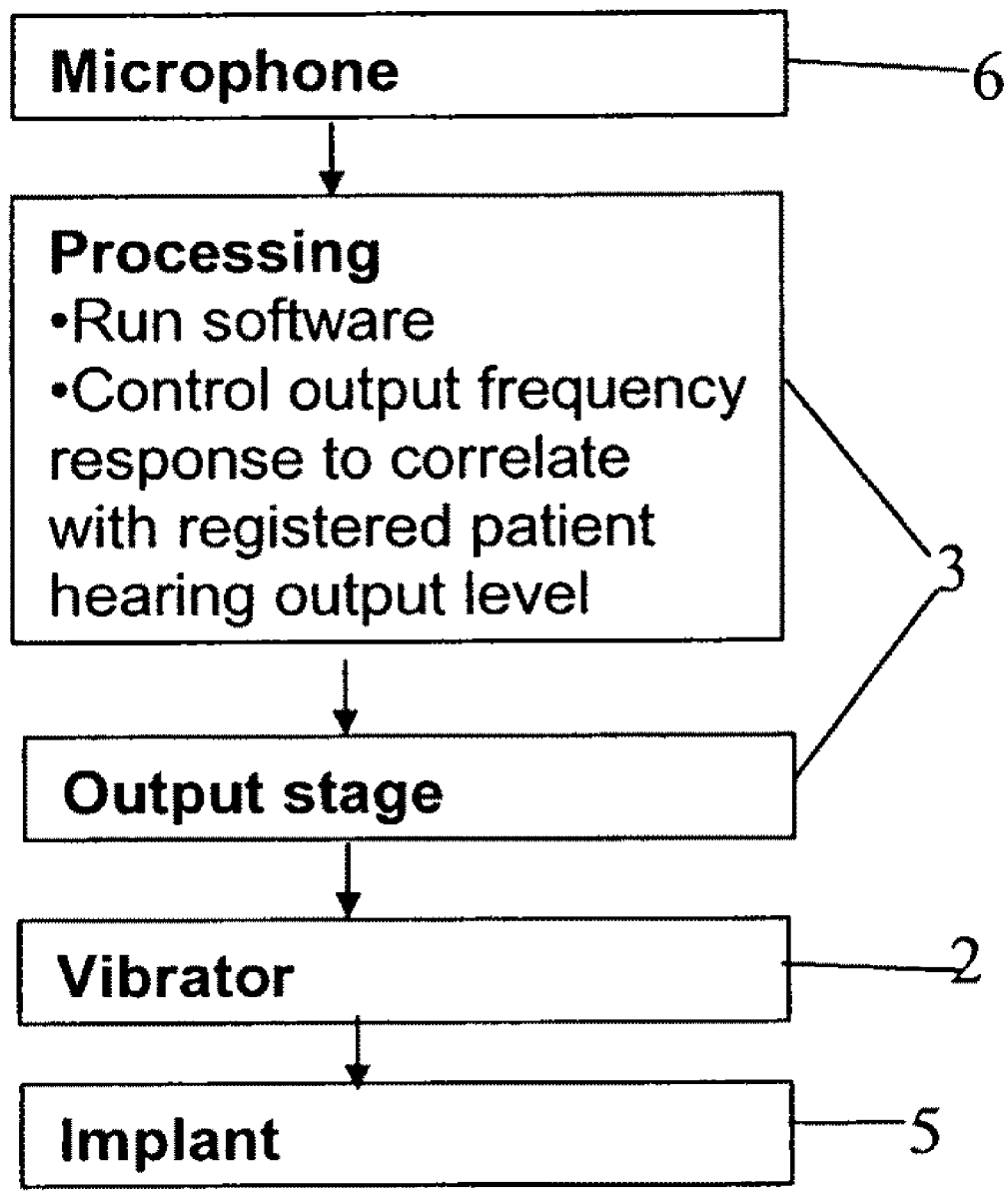
FIG. 3 shows a block diagram of a hearing aid function after fine tuning.

As seen in FIG. 3 this audiogram is then used to fine tune the hearing aid 1 to deliver vibrations to the implant in accordance with the signal picked up by the microphone 6 such that the user will perceive the vibrations as sounds which are above the hearing threshold of the user. This is achieved by programming the hearing aid signal processor 3 to control the output frequency response in accordance with the measurements performed according to FIG. 2.

The invention claimed is:

1. A method for programming a bone integrated bone conducting hearing aid, the method comprising:
    subjecting a hearing aid user to air borne sound and/or to bone transmitted vibrations to collect test results;
    calculating a bone conducting hearing threshold based on the collected test results;
    choosing a bone integrated bone conducting hearing aid based on the calculated bone conducting hearing threshold;
    applying the chosen bone integrated bone conducting hearing aid to a skin penetrating abutment which is firmly attached to a bone integrated fixture in the skull bone of the hearing aid user;
    vibrating a vibrator in the applied bone integrated bone conducting hearing aid at a range of vibration frequencies and amplitudes;
    obtaining the hearing aid user's experienced hearing threshold based on said vibrating of the vibrator in the applied bone integrated bone conducting hearing aid; and
    tuning the chosen bone integrated bone conducting hearing aid for future wearing by the hearing aid user based on the experienced hearing threshold, wherein
    the chosen bone integrated bone conducting hearing aid includes an internal programmable sine-generator, and
    said vibrating includes producing the range of vibration frequencies and amplitudes by the internal programmable sine-generator.

2. The method according to claim 1, wherein the vibrating includes:
    causing the vibrator to vibrate at levels up to an uncomfortable level of the user.

3. A method for programming a bone integrated bone conducting hearing aid, the method comprising:
    subjecting a hearing aid user to air borne sound and/or to bone transmitted vibrations to collect test results;
    calculating a bone conducting hearing threshold based on the collected test results;
    choosing a bone integrated bone conducting hearing aid based on the calculated bone conducting hearing threshold, the chosen bone integrated bone conducting hearing aid including a signal processor, the signal processor including a memory space;
    applying the chosen bone integrated bone conducting hearing aid to a skin penetrating abutment which is firmly attached to a bone integrated fixture in the skull bone of the hearing aid user;
    vibrating a vibrator in the applied bone integrated bone conducting hearing aid at a range of vibration frequencies and amplitudes;
    obtaining the hearing aid user's experienced hearing threshold based on said vibrating of the vibrator in the applied bone integrated bone conducting hearing aid;
    tuning the chosen bone integrated bone conducting hearing aid for future wearing by the hearing aid user based on the experienced hearing threshold; and
    storing in the memory space an audiogram and corresponding hearing/UCL threshold for comparison with later obtained audiograms in order to observe the changes in the clients hearing threshold.

4. The method as claimed in claim 1, further comprising:
    connecting the chosen bone integrated bone conducting hearing aid to a computer having a measurement program installed therein;

providing an input interface including a first button and a second button for the hearing aid user; and detecting input from the hearing aid user through the input interface, including detecting that the hearing aid user pressed a first button when a sound is heard or a second button if a sound is too loud.

5. A bone anchored bone conduction hearing aid system, comprising:

a hearing aid;

a vibrator in the hearing aid;

a fixture anchored in a skull bone of a hearing aid user;

the vibrator being connected to the skull bone via the fixture;

the hearing aid unit having an electronic circuitry;

a push button;

the electronic circuitry having an input interface operable to detect when the hearing aid user presses the push button;

the electronic circuitry having an electronic memory; and the electronic circuitry of the hearing aid having a tone generator and a program embedded in the electronic circuitry operable to perform audiometric measurements via the tone generator and the vibrator connected to the skull and where signal levels from the tone generator and the signals from the push button are storable within the electronic memory.

6. The bone anchored bone conduction hearing aid system according to claim 5 wherein the push button is integrated in the hearing aid.

7. The bone anchored bone conduction hearing aid system according to claim 5 wherein the signal from the push button is transferred by wireless communication to the hearing aid or fitting computer.

8. The method according to claim 1, further comprising:

storing in a memory space of a signal processor of the chosen bone integrated bone conducting hearing aid an audiogram and corresponding hearing/UCL threshold for comparison with later obtained audiograms in order to observe the changes in the clients hearing threshold.

9. The method according to claim 3, wherein the vibrating includes:

causing the vibrator to vibrate at levels up to an uncomfortable level of the user.

10. The method according to claim 3, wherein said vibrating includes:

producing the range of vibration frequencies and amplitudes by an internal programmable sine-generator included in the chosen bone integrated bone conducting hearing aid.

11. The method according to claim 3, further comprising:

connecting the chosen bone integrated bone conducting hearing aid to a computer having a measurement program installed therein;

providing an input interface including a first button and a second button for the hearing aid user; and detecting input from the hearing aid user through the input interface, including detecting that the hearing aid user pressed a first button when a sound is heard or a second button if a sound is too loud.

12. The bone anchored bone conducting hearing aid system according to claim 5, wherein the electronic memory stores an audiogram and corresponding hearing/UCL threshold for comparison with later obtained audiograms.

* * * * *